US00PP28522P2

(12) United States Plant Patent
Hansen

(10) Patent No.: US PP28,522 P2
(45) Date of Patent: Oct. 10, 2017

(54) ***COREOPSIS* PLANT NAMED 'HOT PAPRIKA'**

(50) Latin Name: *Coreopsis verticillata*
Varietal Denomination: Hot Paprika

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/330,027

(22) Filed: Jul. 27, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para

(57) ABSTRACT

The new and distinct threadleaf *coreopsis* plant, *Coreopsis verticillata* plant named 'Hot Paprika', with narrowly-linear, deeply-dissected, typically 3 to 6-lobed foliage of gray-green, numerous flowers of rich deep red ray petals over a prolonged flowering season from early summer until late summer.

1 Drawing Sheet

Botanical designation: *Coreopsis verticillata.*
Cultivar denomination: 'Hot Paprika'.

BACKGROUND OF THE PLANT

The present invention relates to the new and distinct threadleaf *coreopsis* herein also referred to as *Coreopsis* 'Hot Paprika', by the cultivar name, 'Hot Paprika', or as the new plant. The new plant was selected by the inventor in June of 2012 from an isolated block of plants all derived from the seedling with breeder code 10-SRF-COR-312 (not patented) which is a chemically treated seedling of *Coreopsis* 'Route 66' U.S. Plant Pat. No. 20,609 collected in the summer of 2011 from a proprietary unreleased seedling identified with the in the fields of a wholesale perennial grower based in Zeeland, Mich., USA. It was then isolated and compared in subsequent years to other *coreopsis* and subsequently found to be different from all cultivars known to the discoverer.

Asexual propagation at the same nursery in Zeeland, Mich., USA by cuttings has shown 'Hot Paprika' to be stable and reproduce true to type in successive generations.

No plants of *Coreopsis* 'Hot Paprika' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

SUMMARY OF THE PLANT

*Coreopsis* 'Hot Paprika' has not been observed in all possible environmental conditions. The phenotype may vary slightly with changes in environments such as light intensity, fertility, water availability, etc. without, however any variation in genotype.

*Coreopsis* 'Hot Paprika' is distinct from all cultivars known to the inventor in the following traits:

1. Narrow foliage with compact height and dense habit.
2. Heavy flowering of rich deep red ray petals.

3. Flowers produced tightly and densely above the bright-green thin foliage.
4. Long flowering period beginning with concentration in mid-June and continuing until late summer.

Plants of *Coreopsis* 'Hot Paprika' are most similar to 'Center Stage' U.S. Plant Pat. No. 22,707, 'Mercury Rising' U.S. Plant Pat. No. 24,689, 'Limerock Ruby' U.S. Plant Pat. No. 15,455 and 'Red Satin' U.S. Plant Pat. No. 25,736. Both 'Center Stage' and 'Red Satin' are more red-purple in ray flower color and 'Hot Paprika' is more solid rich deep red without purple overtone. Compared to 'Mercury Rising', the new plant is shorter and narrower in habit. Compared to 'Limerock Ruby' the new plant is more winter hard and more branched in habit. *Coreopsis* 'Red Shift' U.S. Plant Pat. No. 20,412 produces ray flower petals that are red at the base and light yellow toward the apex compared to the new plant that has solid red ray petals.

BRIEF DESCRIPTION OF THE DRAWINGS

The color drawings illustrate the overall characteristics of *Coreopsis* 'Hot Paprika' as a three-year-old plant. The colors are as true as reasonably possible given the technology available. The color values may vary slightly depending on light intensity and quality.

DETAILED BOTANICAL DESCRIPTION

Figure 1:
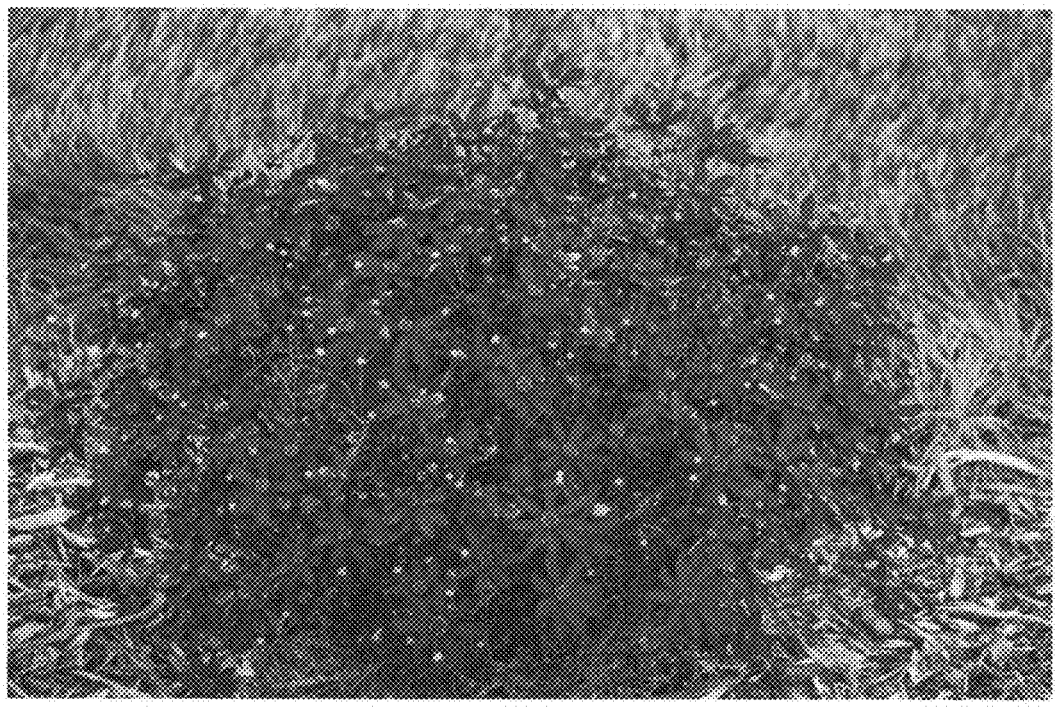
FIG. 1 shows the new plant in a landscape environment.
Figure 2:
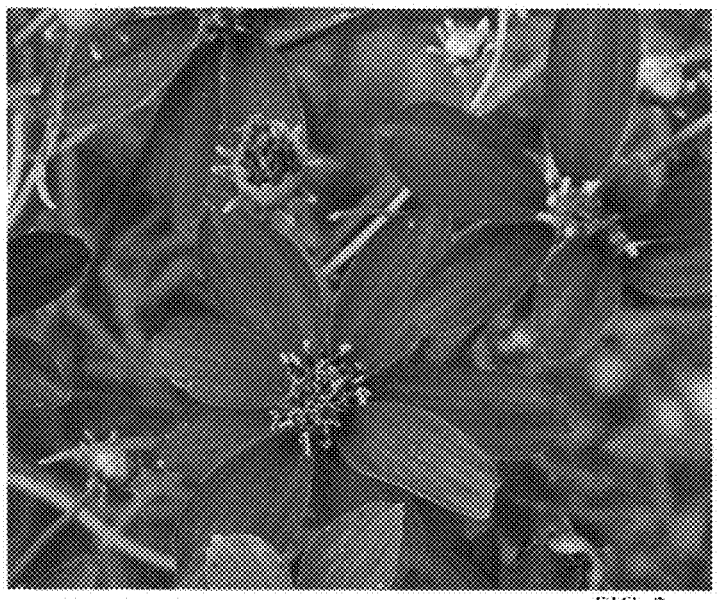
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2001 edition.

Parentage: Female or seed parent 10-SRF-COR-312 (not patented); male or pollen parent unknown.

Asexual propagation: Cuttings, about 10 to 14 days to initiate roots; time to finish as # 1 field grown size about 9 months.

Plant habit: Dense axillary branches; rounded, herbaceous perennial mound; up to 60 cm wide and 32 cm tall; average about 46 cm across and 32 cm tall.

Leaves: Opposite, entire, glabrous; deeply dissected, irregularly lobed, typically tri-lobed, acute apex; base attenuate; sessile; up to 5.9 cm long and 9.5 mm wide, average about 4.5 cm long and 5.0 cm wide; lobes to 8.8 cm long and 2.0 mm across.

Leaf color: Young expanding leaves adaxial nearest RHS 137B and abaxial nearest RHS 137C; mature leaves adaxial nearest RHS 137A, abaxial nearest RHS 137B.

Veins: Pinnate; only abaxial midvein obvious.

Abaxial midveins color: Nearest RHS 137B.

Flower: Composite consisting of ray and disk florets; on terminal branches; about 4.0 cm diameter, about 1.2 cm tall from lower involucral bracts to top of disk florets; attitude upright to outwardly.

Flower fragrance: Not detected.

Phyllary: Sepals in two distinct whorls, outer or lower set consisting of about ten, acute apex, narrowly deltoid, truncate base, glabrous, to about 3.2 mm long and 2.0 mm wide at base; inner or upper set tight against ray petals, usually eight in number, about 6.0 mm long and about 3.0 mm wide, deltoid to ovate; acute apex and truncate base.

Phyllary color: Lower set nearest RHS 137A on both surfaces with lighter margin of nearest RHS 145D; upper set nearest RHS 144A in proximal and central portion of both abaxial and adaxial, marginally and distally nearest RHS 151A.

Flowering period: Early summer until late summer, for about 10 weeks; producing over 40 flowers per stem and over 200 flowers per plant.

Flower longevity: 4 to 6 days.

Flower buds: One to two days before showing ray petal color spherical with slightly flattened top, 4.0 mm wide and 5.0 mm tall.

Flower bud color: Between RHS 163A and RHS 163B.

Stem: Terete; glaucous, thin, wiry, upright attitude, strong, many branched; 4.0 mm wide at base and 23.0 cm long; about seven nodes, average internode spacing about 3.3 cm; spacing about 1.5 cm proximally and to about 4.0 cm in the central portion.

Stem color: Between RHS 137A and RHS 137B.

Peduncle: Terete; glaucous, thin, wiry, strong; average about 0.5 mm in diameter, 3.0 cm long.

Peduncle color: Nearest RHS 137B.

Pedicel: Lacking.

Ray florets: Lacking androecium and androecium.

Ligule: Usually 8 per flower; oblong elongate, glabrous; apex emarginate to two-notched, margin entire; base narrowly cuneate to attenuate; opening flat to form 180° angle; parallel veined; glabrous adaxial and adaxial; about 2.0 cm long and about 9.0 mm wide; basal corolla tube about 1.5 mm to 3.0 mm long and about 0.8 mm diameter; containing only gynoecium with style about 3.0 mm long and split stigma.

Ligule color: Adaxial opening to nearest RHS 53A; abaxial distal half nearest RHS 163B with greenish undertones of nearest RHS 153C and basal half striated between RHS 176A and RHS 153C.

Style color: Of ray floret nearest RHS 184C.

Stigma color: Of ray floret nearest RHS 183A.

Disk florets: 30 to 60 per head; consisting of tepals, staminal tube and pistil; size about 6.0 mm long by 1.0 mm wide at top.

*Petals*.—Five; 5 mm long and 1 mm wide, fused in the basal 4 mm, acute apex.

*Petal color*.—Adaxial blend of nearest RHS 172A and RHS 183A distally and nearest RHS 151D proximally, abaxial blend between nearest RHS 178B and RHS 175C distally and lighter than RHS 153D proximally.

*Staminal tube*.—Made up of five fused stamens, 3 to 4 mm long.

*Anther*.—About 1 mm long, nearest RHS N186A.

*Pollen*.—Fine, round, closest to RHS 15A.

*Style*.—About 4.0 mm long; nearest RHS 163A at base between RHS 22B and RHS 20A distally.

*Stigma*.—Split in half and curling back as it matures; color nearest RHS 23A.

Seed: Linear with slight curve, with acute apex and truncate base; glabrous surfaces; about 4.0 mm long, about 1.5 mm across and about 0.5 mm thick.

Seed color: Variable, nearest RHS 202A. *Coreopsis verticillata* 'Hot Paprika' is tolerant of winter temperatures as low as −20° C. and summer temperatures as high as 40° C. Once established it is also tolerant of dry summer conditions but does best with ample moisture and good drainage. It is not known to be resistant of diseases and pest that are common to other *Coreopsis* cultivars.

I claim:

1. The new and distinct cultivar of *Coreopsis* plant named 'Hot Paprika' as described and illustrated and useful as a specimen landscape plant, mass planting or cut flower.

* * * * *